United States Patent [19]

Wood

[11] Patent Number: 4,731,380
[45] Date of Patent: Mar. 15, 1988

[54] TOLERSTAT AS AN AGENT FOR DIABETIC PERIODONTITIS

[75] Inventor: David D. Wood, Pennington, N.J.

[73] Assignee: American Home Products Corporation (Del.), New York, N.Y.

[21] Appl. No.: 900,557

[22] Filed: Aug. 26, 1986

[51] Int. Cl.$^4$ ............................................. A61K 31/195
[52] U.S. Cl. ...................................... 514/562; 514/900
[58] Field of Search ................................. 514/562, 900

[56] References Cited

U.S. PATENT DOCUMENTS

| | | | |
|---|---|---|---|
| 4,560,794 | 12/1985 | Foster | 560/100 |
| 4,562,286 | 12/1985 | Foster | 560/16 |
| 4,568,693 | 2/1986 | Sestanj et al. | 514/562 |
| 4,590,010 | 5/1986 | Ramachandran et al. | 560/56 |
| 4,590,290 | 5/1986 | Bright | 560/56 |
| 4,604,406 | 8/1986 | Bellini et al. | 514/562 |
| 4,672,058 | 6/1987 | Bellini et al. | 514/62 |
| 4,672,059 | 6/1987 | Bellini et al. | 514/563 |

*Primary Examiner*—Douglas W. Robinson
*Attorney, Agent, or Firm*—John W. Routh

[57] ABSTRACT

A method is disclosed for the prevention and treatment of periodontal disease and alveolar bone loss by administering an effective amount of tolrestat to a human subject.

5 Claims, No Drawings

TOLERSTAT AS AN AGENT FOR DIABETIC PERIODONTITIS

BACKGROUND OF THE INVENTION (a) Field of the Invention

This invention relates to a novel therapeutic use of N-[[5-(trifluoromethyl)-6-methoxy-1-naphthenyl]-thioxomethyl]-N-methylglycine. More specifically this invention relates to a method for the prevention and treatment of periodontal disease in a diabetic human.

(b) Prior Art

The active agent of this invention, N-[[5-(trifluoromethyl)-6-methoxy-1-naphthenyl]-thioxomethyl]-N-methylglycine or a therapeutically acceptable salt thereof, is disclosed in U.S. Pat. No. 4,568,693, issued Feb. 4, 1986. This active agent, hereinafter designated by its generic name tolrestat, previously has been reported to be useful in preventing or relieving diabetic complications such as cataracts, neuropathy, nephropathy and retinopathy (See U.S. Pat. No. 4,568,693). We have now found unexpectedly that tolrestat, either in its free acid form or in its therapeutically acceptable salt form, is useful in the prevention and treatment of periodontal disease in diabetic patients, including alveolar bone loss. This finding, coupled with the fact that tolrestat is a relatively safe drug, renders the method of this invention particularly useful and advantageous.

SUMMARY OF THE INVENTION

According to this invention, a method is provided for reducing the loss of alveolar bone in a diabetic suffering from human periodontal disease. The method comprises administering to the human an effective amount of tolrestat or a therapeutically acceptable salt thereof.

DETAILS OF THE INVENTION

According to the present method, tolrestat, either in its free acid form or in the therapeutically acceptable salt form, is employed as the active agent. Examples of suitable salt forms are described in U.S. Pat. No. 4,568,693 and include the sodium, potassium, magnesium triethylamine and benzylamine salt forms. A preferred salt form is the sodium salt, i.e. tolrestat sodium.

Tolrestat or a therapeutically acceptable addition salt thereof is administered to humans suffering from diabetes mellitus subject to an increased risk of periodontal disease either orally or parenterally. For many reasons oral administration is preferred.

While tolrestat or a therapeutically acceptable salt thereof can be administered alone, e.g. as a sole component of a filled capsule, it is preferred to formulate the compound in various dosage forms for oral or parenteral administration, e.g. tablets or sterile solutions. Such formulations are described in U.S. Pat. No. 4,568,693, herein incorporated by reference in its entirety.

When utilizing tolrestat or one of its above-noted salts in treating periodontal disease, the total dose of active agent can range from 0.1 to 20 mg per kilogram of body weight per day with a preferred dosage range of from 100 to 400 milligrams per patient per day. Generally, a parenteral dose of an oral dose is administered in one to four applications per day. Such doses are considered to be an effective amount when, following their administration, the patient is stabilized or when the progress of the disease has been arrested.

It is well known that humans suffering from diabetes mellitus are subject to periodontal disease of unusual frequency and severity. The cause of this enhanced susceptibility is as yet unknown. Although not intending to be bound by any causal theory, it is apparent that several of the sequellae of polyol accumulation in diabetes may contribute to the enhanced susceptibility to periodonal disease. Microangiopathy of the periodontal tissue with thickening of the capillary basement membrane is a frequent occurence which could retard the extravasation of leukocytes. Tolrestat is known to inhibit such thickening of the capillary basement membranes. Note U.S. Pat. No. 4,568,693. This defect is compounded by a reduction in the inflammatory response characterized by a reduction in the chemotactic response of polymorphonuclear leukocytes and in the response to antigens of lymphocytes. Both of these cellular defects may be caused by the alteration of intracellular polyol and myoinositol concentrations, alterations which are known to be inhibited by tolrestat in the lens, peripheral nervous cord and kidney. Note the above cited U.S. Pat. 4,568,693 at column 1, lines 43–50. Finally, in diabetes there is a reduction of salivary flow of approximately two-thirds accompanied by a compensatory enlargement of the parotid gland. This parotid defect has been attributed to both degenerative changes in the autonomic nerve innervating the gland and to alterations in the metabolic pathways required for the synthesis of salivery mucoproteins. In either case there is a basis for expecting that tolrestat would amelioiate the pathology. Note U.S. Pat. No. 4,568,693. It is assumed that the efficacy of tolrestat in periodontitis is a consequence of its combined effects on each of the principal pathologies which combine to accelerate periodontal disease. In any event, diabetic human beings, when administered tolrestat, are significantly more resistant to periodontal disease and the attendant loss of alveolar bone than are diabetic humans not being administered tolrestat.

I claim:

1. A method for treating periodontal disease in a diabetic human subject which comprises administering to the human a therapeutically effective amount of tolrestat or a therapeutically acceptable salt thereof.

2. The method of claim 1 in which the effective amount of tolrestat is within the range of from 0.1 to 20 mg kilogram of body weight.

3. The method of claim 1 in which the effective amount of tolrestat is within the range of from 100 to 400 milligrams per day.

4. The method of claim 1 in which the therapeutically acceptable salt is the sodium salt.

5. The method of claim 1 in which the human being treated suffers from diabetes mellitus.

* * * * *